United States Patent
Schütz et al.

(10) Patent No.: US 12,274,610 B2
(45) Date of Patent: Apr. 15, 2025

(54) WOUND DRESSING WITH ODOR CONTROL PROPERTIES

(71) Applicant: Essity Hygiene and Health Aktiebolag, Gothenburg (SE)

(72) Inventors: Patrick Schütz, Hamburg (DE); Sören Lafendt, Hamburg (DE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 18/689,120

(22) PCT Filed: Oct. 5, 2021

(86) PCT No.: PCT/EP2021/077475
§ 371 (c)(1),
(2) Date: Mar. 5, 2024

(87) PCT Pub. No.: WO2023/057051
PCT Pub. Date: Apr. 13, 2023

(65) Prior Publication Data
US 2024/0269016 A1  Aug. 15, 2024

(51) Int. Cl.
*A61F 13/15* (2006.01)
*A61F 13/84* (2006.01)

(52) U.S. Cl.
CPC .. *A61F 13/8405* (2013.01); *A61F 2013/8423* (2013.01)

(58) Field of Classification Search
CPC ...... A61F 13/8405; A61F 13/00; A61F 15/00; A61F 2013/00089; A61F 2013/00361; A61F 2013/00523; A61F 13/00748
See application file for complete search history.

(56) References Cited

U.S. PATENT DOCUMENTS

| | | | |
|---|---|---|---|
| 10,245,346 B2 | 4/2019 | Locke et al. | |
| 2005/0106980 A1* | 5/2005 | Abed | B32B 27/34 442/361 |
| 2014/0249495 A1* | 9/2014 | Mumby | A61F 13/0226 604/385.01 |
| 2015/0157758 A1* | 6/2015 | Blucher | A61L 15/44 424/409 |
| 2018/0193514 A1 | 7/2018 | Kim et al. | |

(Continued)

FOREIGN PATENT DOCUMENTS

| | | |
|---|---|---|
| CN | 1037646 A | 12/1989 |
| CN | 1426315 A | 6/2003 |
| CN | 102105123 A | 6/2011 |

(Continued)

OTHER PUBLICATIONS

Chinese Application No. 202180101718.8; Office Action with English translation dated Apr. 25, 2024; 20 pgs.

(Continued)

*Primary Examiner* — Jacqueline F Stephens
(74) *Attorney, Agent, or Firm* — CANTOR COLBURN LLP (57) ABSTRACT

A wound dressing is provided, comprising a wound facing layer an opposing backing layer and a layered, interior arrangement positioned therebetween. The interior arrangement comprises an absorbent core, an activated carbon containing layer and a zeolite containing layer.

20 Claims, 3 Drawing Sheets

(56) References Cited

U.S. PATENT DOCUMENTS

2019/0351094 A1* 11/2019 Maher .................... A61L 15/46
2020/0155355 A1   5/2020 Hill et al.

FOREIGN PATENT DOCUMENTS

| | | | | |
|---|---|---|---|---|
| CN | 102271720 | A | 12/2011 | |
| CN | 105492032 | A | 4/2016 | |
| CN | 105963074 | A | 9/2016 | |
| CN | 106999304 | A | 8/2017 | |
| CN | 110099653 | A | 8/2019 | |
| CN | 110913811 | A | 3/2020 | |
| CN | 113116634 | A | 7/2021 | |
| CN | 113242724 | A | 8/2021 | |
| EP | 1985270 | A2 | 10/2008 | |
| EP | 3315145 | A1 | 5/2018 | |
| GB | 2531345 | A * | 4/2016 | ....... A61F 13/00008 |

OTHER PUBLICATIONS

International Search Report & Written Opinion for International Application No. PCT/EP2021/077475; International Filing Date: Oct. 5, 2021; Date of Mailing: Jul. 1, 2022; 11 pages.
Decision of Rejection by the National IP Administration of the People's Republic of China (CNIPA) issued Jun. 6, 2024 for Chinese Application No. 202180101718.8, with English translation, 17 pages.
Mexican Application No. MX/a/2024/004099; Office Action with English translation dated Aug. 28, 2024; 20 pages.

\* cited by examiner

WOUND DRESSING WITH ODOR CONTROL PROPERTIES

CROSS REFERENCE TO RELATED APPLICATIONS

This application is a National Stage application of PCT/EP2021/077475, filed Oct. 5, 2021, which is incorporated by reference in its entirety herein.

TECHNICAL FIELD

The present disclosure relates to a wound dressing including a wound facing layer, an opposing backing layer and an interior layered arrangement including an absorbent core positioned therebetween.

BACKGROUND

When skin or other tissue is wounded, the wound usually starts emitting exudate. The exudate includes liquid leaking out of blood vessels and may contain serum, fibrin, and leukocytes. Wounds which include areas of strong infection or inflammation can exude high fluid volumes. To manage these volumes, the wounds are often covered with wound dressings that include an absorbent core positioned between a wound facing layer and a backing layer.

The absorbent cores can for example include super absorbent particles, such as described in e.g. EP 1985270. The absorbent core can take up substantial amounts of fluid.

Absorbent wound dressings such as described above can be put on the wound and left there for a significant time. However, this may result in production of odors stemming inter alia from bacterial growth in the wound but also in the absorbed wound exudate. The odors tend to have an unpleasant smell and can lead to social isolation of the patient due to feelings of embarrassment, for example preventing the person with the wound from participating in social activities. Also, the odors may force the wound dressings to be changed often, possibly also more often than optimal from a wound management perspective, leading both to higher cost and to sub-optimal wound healing.

There is consequently a need in the art to provide wound dressings addressing the above-mentioned issues.

SUMMARY

The present inventors have found that a wound dressing as defined herein or produced according to the method defined herein, provides advantageous properties in relation to the perceived intensity of odors from wounds.

In one aspect, the present disclosure therefore provides a wound dressing including a liquid permeable wound facing layer, an opposing backing layer, and a layered, interior arrangement positioned therebetween. The interior layered arrangement includes an absorbent core, an active carbon containing layer and a zeolite containing layer.

Wound dressings of the present disclosure have been shown to reduce the perceived odor from the wound site and/or dressing, while being able to be kept on the wound for prolonged periods of time. The wound dressing of the present disclosure may also be relatively thin.

The active carbon containing layer and the zeolite containing layer may for example be arranged between the absorbent core and the backing layer, providing for improved odor control properties, e.g. also being able to handle odors emanating from wound exudates absorbed in the absorbent core.

In another aspect, the present disclosure provides a method for the production of a wound dressing, including the steps of positioning an absorbent core, an active carbon containing layer and a zeolite containing layer between a wound facing layer material and a backing layer material; and joining the wound facing layer material to the backing layer material forming a seam encircling the absorbent core, active carbon containing layer and zeolite containing layer.

These and further aspects will now be described in more detail with reference to the appended drawings

DETAILED DESCRIPTION

Figure 1:
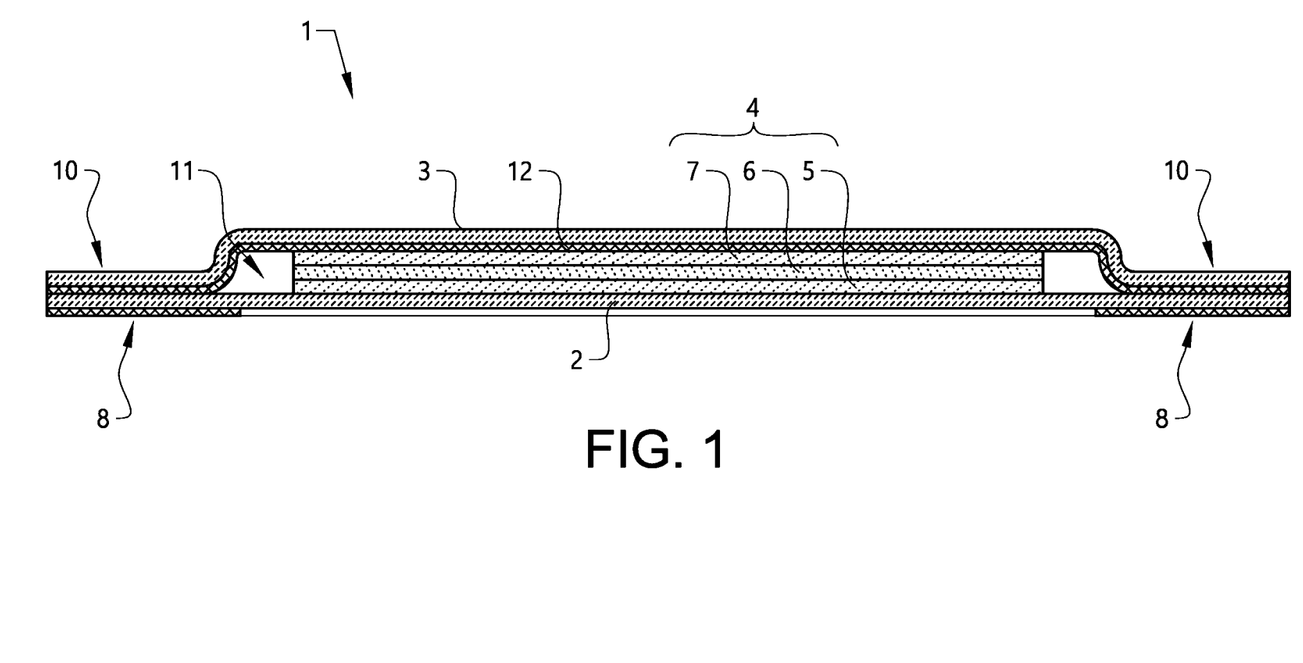
FIG. 1 schematically shows a cross-sectional view of a wound dressing
Figure 2:
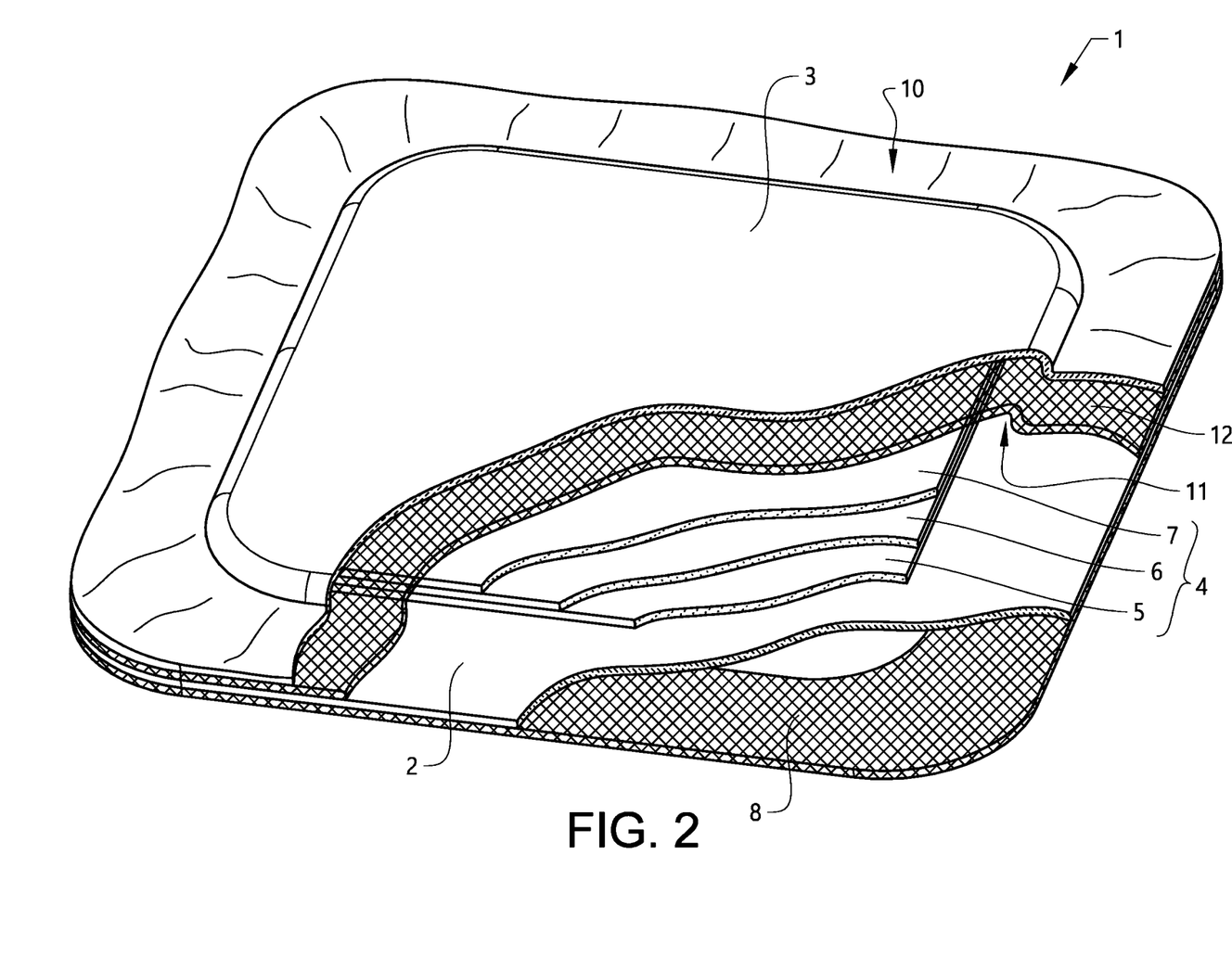
FIG. 2 schematically shows a sectional perspective view of a wound dressing
Figure 3:
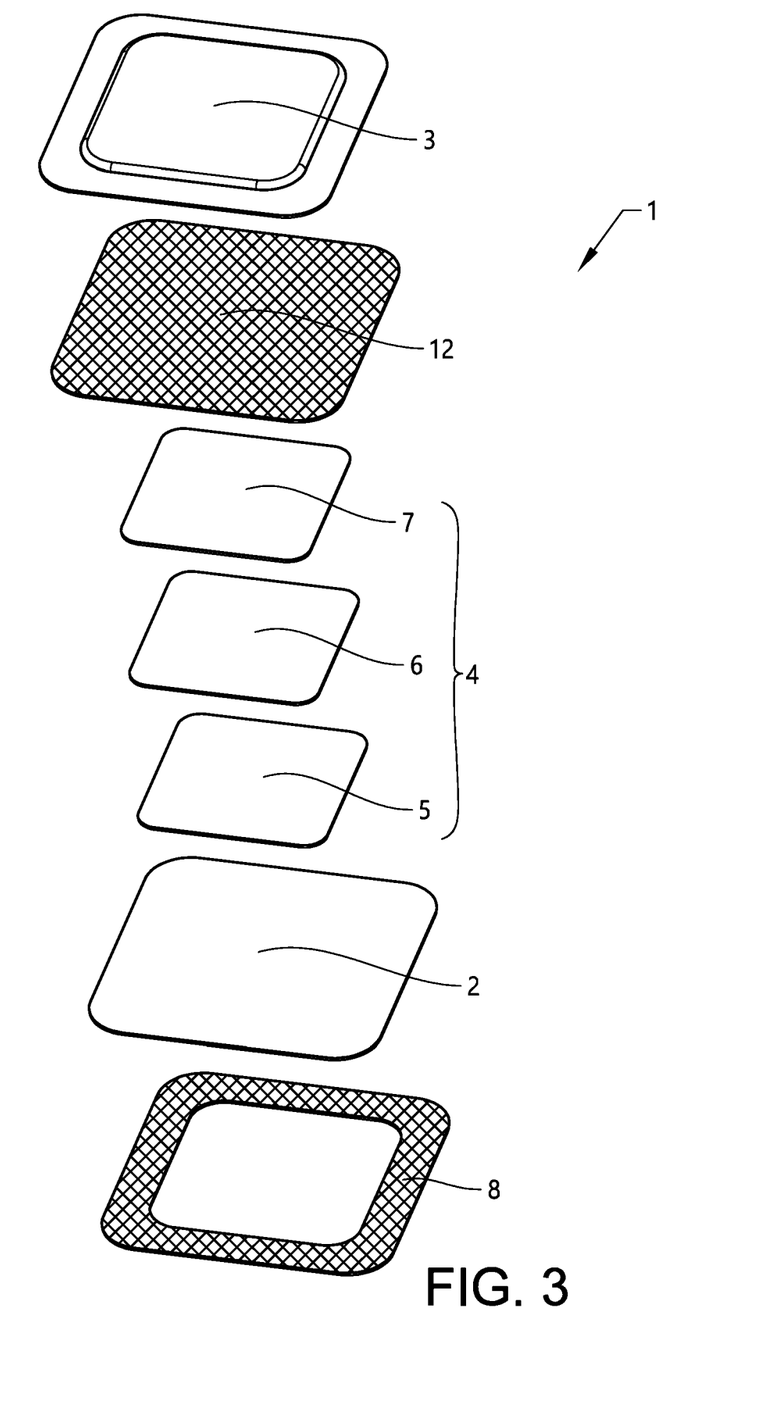
FIG. 3 schematically shows an exploded perspective view of a wound dressing

One embodiment of a wound dressing according to the present disclosure is illustrated in FIGS. 1 to 3.

The illustrated wound dressing 1 includes a wound facing layer 2, an opposing backing layer 3 and a layered arrangement 4 positioned between the wound facing layer and the backing layer. The layered arrangement 4 includes an absorbent core 5, an active carbon containing layer 6 and a zeolite containing layer 7.

The wound dressing 1 is adapted to be placed on a wound with the wound facing layer 2 towards the wound surface and the opposing, backing layer 3 facing away from the wound surface.

The wound dressing 1 is relatively flat, having a sheet like structure with its main extension in the X-Y plane while being comparatively thin in the Z (thickness) direction.

While being illustrated having a rectangular shape (outer contour in the X-Y-plane, when seen from above flattened out on a flat surface) in FIG. 2, wound dressings according to the present disclosure may be made in different sizes and shapes. For example, the dressing may have a rectangular, square, round, or trapezoidal outer contour. While not limited to any specific size, the surface area of the wound dressing 1 (i.e. the area covered by an unused wound dressing flattened out on a flat surface) may for example be in the range of from 5 to 1000 $cm^2$, such as from 25 to 200 $cm^2$. The size and shape of the dressing may be selected to match the size and shape of the wound it is intended to cover.

As in the wound dressing of FIGS. 1 and 2, the wound facing layer 2 and the backing layer 3 may be permanently joined together by means of a seam 10 to form an inner portion 11 in which the interior, layered arrangement 4 is positioned. The seam 10 may be obtained by means of adhesives, heat fusion, ultrasonic welding, etc.

The seam 10 defines an inner portion 11, laterally inside the seam, in which the wound facing layer 2 and the backing layer 3 are not joined, or at least not permanently joined, and in which the interior, layered arrangement 4 is disposed, between the wound facing layer 2 and the backing layer 3.

By the term "not permanently joined" as used herein is meant that parts of the wound facing layer 2 and the backing layer 3 within the seam 10 may be loosely attached to each other in the inner portion 11, but only to such an extent that they can become detached from one another by means of swelling of the absorbent core 5 due to absorption of liquid, as will be described later. On the other hand, in the seam 10, the wound facing layer 2 and the backing layer 3 are not able to be detached from one another by means of such swelling of the absorbent core 5, i.e. they are to be considered "permanently joined" in the area of the seam 10.

The width of the seam 10 may for example have a width of from 0.5, 0.8 or 1, to 3, 2 or 1.5 cm. The width of the seam may be the same around the entire circumference of the wound dressing or may differ in different portions.

The seam 10 may be liquid proof, i.e. such that liquid may not be able to leak out from the inner portion 11 to the exterior of the wound dressing 1 laterally through the seam 10, e.g. between the wound facing layer 2 and the backing layer 3.

The layered arrangement 4 may be freely movable within the inner portion 11 of the wound dressing 1, or may be fixedly attached therein, such as by attaching the layered arrangement 4 to the wound facing layer 2 or the backing layer 3.

The layered arrangement 4, i.e., absorbent core 5, carbon containing layer 6 and zeolite containing layer 7 may be adapted to the wound dressing 1, such that it is possible, in an unused wound dressing 1 to position the layered arrangement such that its outer perimeter does not lie against the perimeter of the inner portion 11, but always lie laterally inside the perimeter of the inner portion. This may ensure the ability for especially the absorbent core 5 to swell within the inner portion 11 without being sterically restricted by the perimeter of the inner portion 11.

The shape of the inner portion 11 may be similar to the outer contour of the dressing 1, e.g. a rectangular inner portion for a rectangular wound dressing. However, the inner portion may also take a different shape than the outer contour of the wound dressing, e.g. a circular inner portion in a square wound dressing.

As illustrated in FIGS. 1 and 2, the inner portion 11 may be formed by a seam 10 encircling the inner portion that joins together the wound facing layer 2 and the backing layer 3, where the wound facing layer 2 and the backing layer 3 are made out of different pieces of material. However, it is also contemplated that the wound facing layer and the backing layer can be made out of one and the same piece of material that is folded, with the layered arrangement (core, carbon containing layer and zeolite containing layer) positioned within the fold, and a seam forming the non-fold perimeter of the inner portion.

Materials suitable for a wound facing layer for use in a wound dressing in accordance with the present disclosure, such as the wound facing layer 2 in the illustrated embodiment, are such that are suitable for being placed towards a wound and that are permeable to liquid wound exudates. Properties that are advantageous for such materials include a low tendency to adhere to the wound bed, high biocompatibility, and that it can easily be removed from wet wound tissue. Examples include, but are not limited to non-woven materials, such as based on polypropylene, perforated polymer films and porous or perforated silicone-based materials, being commonly used in the art. The wound facing layers used in commercially available wound dressings, such as the Cutimed-range of wound dressings from Essity (Hamburg, DE) represent non-limiting suitable examples.

Materials suitable for a backing layer for use in a wound dressing in accordance with the present disclosure, such as the backing layer 3 in the illustrated embodiment, are such that can be joined, directly or indirectly, with the wound facing layer to provide a seam and an inner portion for housing the layered, internal arrangement. By indirectly joined is meant two layers being joined together using an intermediate material, such as for example an adhesive layer or adhesion promoting layer, there between.

Examples of backing layer materials include materials also suitable as the wound facing layer, such as non-woven. However, it may be desirable that the backing layer is made of a liquid impermeable material, such as a liquid impermeable but vapor permeable (i.e. breathable) material. This would for instance allow the patient to shower when wearing the dressing. Examples of suitable backing layer materials that can be provided as breathable materials include polyurethane and co-polyester based films.

The backing layer may be of an elastically or plastically stretchable nature. When the liquid absorbent core, to be described below, swell upon absorption of liquid, a plastically or elastically stretchable backing layer may adhere to the shape of the layered, internal arrangement. By this, the backing layer better accommodate the internal arrangement and to reduce the tendency of the wound facing layer to bulge out towards the wound surface due to the swelling of the absorbent core.

In wound dressings according to the present disclosure, an absorbent core is provided to absorb and hold liquid wound exudates. The core can be up of any suitable absorbent or fluid-absorbing material as known in the art. In the illustrated embodiment the absorbent core 5 is positioned between the wound facing layer 2 and the active carbon containing layer 6.

The absorbent core may include suitable amounts of superabsorbent particles (SAP) to provide the desired absorption capacity of the absorbent core. Such superabsorbent materials are well known and constituted by a water-swellable and water-insoluble material which is capable of absorbing large quantities of fluid upon formation of a hydrogel. Exemplary superabsorbent materials are based on cross-linked acrylic acid-based polymers. Superabsorbent materials are capable of absorbing fluids of at least 10 times its own weight, such as at least 100 times its own weight. The amount of said superabsorbent particles may be at least 10% by weight, such as from 10, 20, 30 or 40 to 50, 60, 70 or 80 wt % based on the total dry weight of the absorbent core.

As an example, the absorbent core may include of a mixture of airlaid cellulose fibres and SAP (super absorbent particles) where the SAP constitutes from 10, 20, 30 or 40 to 50, 60, 70 or 80 wt % of the dry weight of the absorbent core, such as about 50 wt %.

Upon swelling, the absorbent core may swell, predominantly in its thickness dimension, and may when saturated be significantly thicker, such as e.g. 5 to 10 times thicker, than in dry state. For that purpose, it is advantageous that the absorbent core 5, in dry state, has a surface area that is smaller than the surface area of the inner portion so as to allow for the absorbent core to swell without being sterically hindered within the inner portion. For example, the surface area of the absorbent core may be from 40, 50, 55 or 60 to 90, 80 or 70% of the surface area of the inner portion.

In dry state, before swelling, the absorbent core may be a flat layer having a thickness of from 0.5, 2 or 3 to 10, 7 or 5 mm. Carbon containing layer 6

A wound dressing according to the present disclosure includes an active carbon containing layer.

In the illustrated embodiment, an active carbon containing layer 6 is provided, positioned between the absorbent core 5 and the backing layer 3.

The intention of introducing an active carbon containing layer in a wound dressing of the present disclosure is to reduce the odor burden of the wound by entrapping VOCs (Volatile Organic Compounds) by means of adsorption. Such active carbon containing layer may include a carrier material that carries the active carbon particles. The active carbon particles may for example being coated or deposited on, impregnated or integrated in the carrier material. The carrier material may be a liquid- and gas-permeable material, such as a foam, for example a polyurethane based foam, or a non-woven or textile material of natural and/or synthetic fibers.

As used herein, the term "active carbon" refers to the standard understanding of the term (also known as activated carbon), i.e. a microcrystalline, non-graphitic form of carbon which has been processed to increase internal porosity.

The active carbon in an active carbon containing layer may have a mean pore size according to ISO15901 of from 0.5 to 100 nm.

The active carbon in the active carbon containing layer may have a specific surface area (BET) of from 500 to 5000 $m^2/g$ for example about 3000 $m^2/g$.

The particle size of the active carbon may suitably be from 2 to 50 μm, such as from 6 to 12 μm.

The basis weight of active carbon in the active carbon containing layer may be from 30, 50 or 100 to 500, 300 or 200 $g/m^2$.

The active carbon content in the active carbon containing layer may be from 50 to 400 wt % compared to the weight of the carrier material.

The thickness of the active carbon containing layer may be in the range of from 0.1, 0.2, 0.5 or 1, to 5, 4, 3 or 2 mm.

A wound dressing according to the present disclosure further includes a zeolite containing layer.

In the illustrated embodiment, a zeolite containing layer 7 is positioned between the active carbon containing layer 6 and the backing layer 3.

As used herein, the term "zeolite" refers to the standard understanding of the term according to Smith (Smith, J. V., 1963. Structural classification of zeolites, Mineral. Soc. Am., Spec. Paper, 1, 281-290.) i.e., an aluminosilicate with a frame-work structure enclosing cavities occupied by large ions and water molecules, both of which have considerable freedom of movement, permitting ion exchange and reversible dehydration. For the purposes of the present disclosure, it is preferred that the zeolites in the zeolite containing layer are free, or substantially free, from silver.

The intention of introducing a zeolite containing layer into a wound dressing of the present disclosure is to reduce the odor burden of the wound by entrapping VOCs (Volatile Organic Compounds) by means of adsorption. The zeolites have a different chemical composition and physical configuration from that of the active carbon, such as a different average pore size. It is thought that the zeolites may be able to absorb different substances than the active layer, resulting in overall advantageous adsorption properties of the wound dressing.

The zeolites in the zeolite containing layer may for example have a mean pore size of from 0.1 to 1 nm, such as from 0.2 or 0.3 to 0.8 or 0.6 nm, for example about 0.4 nm, as is measured by ISO15901

The zeolites in the zeolite containing layer may for example have a specific surface area (BET) of from 100 to 1000 $m^2/g$, such as from 200 or 300 to 800 or 600 $m^2/g$, for example about 500 $m^2/g$.

The concentration/basis weight of zeolite in the zeolite containing layer may be at least 0.2 $g/m^2$, such as in the range of from 0.2, 0.5, 1 or 2, to 10, 8, 6 or 4 $g/m^2$, for example about 2 $g/m^2$.

The thickness of the zeolite containing layer may be in the range of from 0.1, 0.2, 0.5 or 1, to 5, 4, 3 or 2 mm.

One example of a commercially available zeolite containing material for use in a wound dressing according to the present disclosure is the zeolite component of the product LavaXL® from Sciessent, LLC (MA, US).

The zeolite containing layer may include a carrier material and zeolite particles carried by the carrier material. The zeolite particles may for example be coated or deposited on, impregnated or integrated in the carrier material. The carrier material may be a gas permeable material, such as a foam, for example a polyurethane based foam, a non-woven or a textile material of natural and/or synthetic fibers, such as for example a stitch bond polyester web, onto which the zeolite carbon particles may be deposited.

As in the illustrated embodiment, the zeolite containing layer may advantageously be positioned between the active carbon containing layer and the backing layer. It may be advantageous to have the active carbon containing layer to be the first material to adsorb VOC-s, to enable the zeolite containing layer to adsorb the VOC-s that passed un-adsorbed through the active carbon containing layer.

In an alternative configuration, where the zeolite containing layer may be positioned between the absorbent core and the active carbon containing layer, the VOC-s that are not adsorbed by the zeolite layer may be more difficult to adsorb using active carbon, requiring more active carbon such as a thicker layer or a layer with higher carbon loading to obtain the same odor reducing effect.

The zeolite containing layer and/or the active carbon containing layer may advantageously contain further odor control active components different from zeolites and active carbon. Examples of such odor control active components include e.g. zinc oxides, cyclodextrine, triclosan etc. The zeolite containing layer and the active carbon containing layer are preferably substantially free from silver or silver-based constituents.

In further alternatives, more than one carbon containing layer and/or more than one zeolite containing layer can be present between the absorbent core and the backing layer, for example in a CCZZ (carbon-carbon-zeolite-zeolite) or CZCZ-configuration.

The thickness of the active carbon containing layer and the zeolite containing layer should be made as small as possible while meeting the desired performance requirements. The total thickness of carbon containing layer(s) and zeolite containing layer (s), as measured in dry state without compressing the layers, may for example be in the range of from 0.5 to 5 mm, such as from 1 to 3 mm.

As in the illustrated embodiment, the absorbent core 5, the active carbon containing layer 6 and the zeolite containing layer 7 in a wound dressing 1 of the present disclosure may have similar size and shape. Alternatively, one or two of the absorbent core 5, the active carbon containing layer 6 and the zeolite containing layer 7 may have a size and/or shape that is different from the other components in the layered arrangement. As illustrated in FIGS. 1 and 2, the absorbent core 5, active carbon containing layer 6 and zeolite containing layer 7 may essentially completely overlap each other.

Wound dressings of the present disclosure may be void of any active carbon and/or zeolite being intentionally positioned between the absorbent core and the wound facing layer.

An active carbon containing layer suitable for use in accordance with the present disclosure may contain substantially no zeolites in its composition or may include active carbon and zeolite in the weight ratio carbon:zeolite in the range of from 1:0 to 5:1.

A zeolite containing layer suitable for use in the accordance with the present disclosure may contain substantially no active carbon in its composition or may include active zeolite and carbon in the weight ratio zeolite:carbon in the range of from 1:0 to 5:1.

As in the illustrated embodiment, a bond promotion material 12 may be provided between the wound facing layer 2 and the backing layer 3, at least in the areas corresponding to the seam 10, in order to improve the ability of forming a strong bonding between the wound facing layer 2 and the backing layer 3 in the seam 10.

The bond promotion material 12 may for example be provided as separate film or web, or that is applied to either one or both of the wound facing layer 2 and the backing layer 3, e.g. by spray coating, swirl spraying or curtain coating.

The bond promotion material 12 may include or consist of a hot melt adhesive that is that essentially solid in room temperature and tacky at higher temperatures, e.g. a co-polyamide or co-polyester adhesive.

As illustrated in FIG. 1, the bond promotion material 12 may be provided in the area of the seam 10 and also the inner portion 11, being positioned between the internal arrangement 4 and the backing layer 3.

Alternatively, the bond promotion material may be provided in the area of the seam and also in the inner portion, in which it is positioned between the internal arrangement and the wound facing layer.

The bond promotion material may be liquid permeable to allow transfer of liquid, such as wound exudates, from the wound facing layer into the absorbent core. For example, the bond promotion material may be provided as a net or web of fiberized hot melt adhesive.

In yet another alternative, the bond promotion material may be provided in the area of the seam, whereas it is being essentially non-present in the inner portion.

An example of a material for the bond promotion material suitable for use in a wound dressing of the present disclosure is commercially available as MED2123R from Avery Dennison, BE, being a web of hotmelt rubber adhesive.

In yet another alternative, a wound dressing of the present disclosure does not contain any such bond promotion material.

As in the illustrated embodiment, an adhesive material 8 may be disposed on at least part of the wound facing side of the wound facing layer 2. The adhesive material 8 is intended for attaching the wound dressing 1 to a user. Such skin adhesive 8 may be arranged as a perimeter forming a window for allowing transport of wound exudates through the wound facing layer without being impeded by the skin adhesive. Adhesives suitable for use include those that are skin friendly and known for the purpose of adhering a wound dressing to the skin of the wearer.

The adhesive material described above is optional, and wound dressings according to the present disclosure may alternatively be void of such adhesive material. Wound dressings according to the present disclosure, without such adhesive material are instead intended to be fixated at the wound site by an external fixation means, such as, but not limited to fixation tapes marketed under the Leukoplast® or Fixomull® tradenames, by means of a gauze, a wrap or by other means known to the person skilled in the art as being suitable for fixating wound dressings onto wounds.

The present disclosure also relates to a method for the production of a wound dressing, such as the wound dressing 1 discussed above. It is to be understood that all details discussed above for the wound dressing 1 and its components are also applicable to this method.

As can be understood from FIG. 3, the method includes arranging the layers of a wound dressing on top of each other and combining them into the wound dressing.

A method of the present disclosure includes the step of positioning an absorbent core 5, an active carbon containing layer 6 and a zeolite containing layer 7 between a wound facing layer material 2 and a backing layer material 3, and joining the wound facing layer material 2 to the backing layer material 3 to form a seam 10 encircling the absorbent core 5, the active carbon containing layer 6 and the zeolite containing layer 7.

The absorbent core 5, active carbon containing layer 6 and zeolite containing layer 7 may be provided separately or may be pre-joined and positioned between the wound facing layer 2 and the backing layer material 3 as a pre-assembled unit.

As the wound dressing may further include optional components such as the bond promotion layer 12 and the adhesive material 8, the method may consequently also include arranging these components as desired.

For example, a bond promotion layer, if present, may be pre-joined to the wound facing layer material or the backing layer material prior to assembly of the wound dressing, or may be provided as a separate layer into the assembly step. The adhesive material, if present, may be pre-joined to the wound facing side of the wound facing material prior to assembly of the wound dressing, or may be provided after the step of joining the wound facing layer material to the backing layer material. It is to be understood that "joining the wound facing layer to the backing layer material" herein includes both direct joining, i.e. without any intermediate layer, or indirect joining, i.e. in the presence of an intermediate layer, such as a bond promotion layer material.

Experiments

A comparative study was performed to determine the odor threshold values of artificial wound odor diffusing though five different types of wound dressings.

The following five wound dressings were used in this comparison:
1. Vliwaktiv®, 10×10 cm, Lohmann Rauscher
2. Curea P1 DUO active, 10×10 cm, Curea Medical
3. Sorbion® Sachet S, 10×10 cm, BSN Medical
4. Carbonet®, 10×10 cm, Smith&Nephew
5. Prototype, 10×10 cm An exemplary prototype was composed of a 40 gsm (gram per square meter) PP nonwoven as wound facing layer, a 700 gsm SAP/cellulose tissue absorbent core, a 150 gsm polyurethane foam loaded with about 150 gsm active carbon as the active carbon containing layer, a 100 gsm stich bond PES web coated with approx. 2 gsm Zeolite (LavaXL® from Sciessent) as the zeolite containing layer, and a 25 μm poly-urethane film as the backing layer.

An aqueous malodor solution containing inter alia dimethyltrisulfide, isovaleraldehyde and butyric acid, intended to mimic the malodor produced by wounds, was used.

For each type of wound dressing sample, a stainless-steel plate with a round cavity of 50 ml volume was used. 50 ml of the malodor solution was put into the cavity and the respective wound dressing sample was fixed to the plate to cover the cavity, using adhesive bandage (Fixomull®, Essity, Hamburg, DE), to create an evaporation area with 8 cm side length each.

Each preparation (plate with dressing) was put into separate Nalophan® sampling bags and filled with 50 l neutral air by using a mass flow controller.

The bags were stored at 37° C. in a climate chamber for 24 hours before evaluation.

After the storage period, the sample air was transferred into three 10 l Nalophan bags per preparation in order to carry out a triple analysis.

A study of the odor reducing ability wound dressings was performed by performing test of Odor Concentration (EN 13725:2003), Odor Intensity (VDI 3882-1) and Hedonic Tone (VDI 3882-2 and ISO 16000-28 (D))

The direct evaluation is carried out with a PureSniff device from Olfasense GmbH offering the same volume flow to all panel members.

Odor Concentration

Procedure

The odor concentration of gaseous samples of odorants was determined according to European standard method EN13725 by using an olfactometer to repeatedly present a panel of selected and screened human subjects with a sample, in varying dilutions with neutral odor free air.

The measurement process is computer controlled. A panel of 4 panel members participated in each test. At each presentation of the diluted sample the panel member was asked to indicate whether they detect an odor or not. Following this procedure, the individual detection threshold estimate (ITE) for each panel member is determined repeatedly. This is the dilution $Z_{ITE}$ between a presentation where the panel member cannot smell the odor, and presentations at dilutions where they can consistently detect the odor.

The odor concentration of the tested sample is then calculated as the geometric mean of all the $Z_{ITE}$ values of all the panel members. A minimum of 8 $Z_{ITE}$ values is required for one measurement Because all the panel members are selected for their ability to detect a standard reference odor, n-butanol, it is assumed that the odor stimulus at the detection threshold for that panel member during the test is equivalent to the defined standard reference stimulus for n-butanol, used for panel selection.

The unit of measurement of 1 $ou_E \cdot m^{-3}$ is defined as equal to the smell of 123 $\mu g \cdot m^{-3}$ of n-butanol.

When the mean dilution factor applied to reach the detection threshold for a sample is calculated to be x, the odor concentration is x $ou_E \cdot m^{-3}$ at standard conditions for olfactometry (20° C., wet)

The standard imposes strict statistical performance criteria, for accuracy and precision under repeatability conditions, which are checked continuously using reference odorant mixtures. Panel members are checked frequently and are excluded from the test when their ability to detect smells is no longer in compliance with fixed selection criteria.

Results

The odor concentration results are reported in table 1 below

TABLE 1

| | Odor concentration | | |
|---|---|---|---|
| Sample | Mean value $ou_E/m^3$ | Lower limit (95%) $ou_E/m^3$ | Upper limit (95%) $ou_E/m^3$ |
| 1 | 3158 | 2581 | 3864 |
| 2 | 3165 | 2587 | 3872 |
| 3 | 19661 | 16070 | 24055 |
| 4 | 1644 | 1325 | 2040 |
| 5 (exemplary embodiment of this disclosure) | 316 | 255 | 392 |

Odor Intensity and Hedonic Tone

Procedure

The evaluation of the intensity the category scale with 7 on the bases of VDI 3882-1 is used, see Table 2. For the evaluation process the panelist correlated the intensity description to the odor impression.

TABLE 2

| Scale of Odor Intensity | |
|---|---|
| Description | Intensity Level |
| Extremely strong | 6 |
| Very strong | 5 |
| Strong | 4 |
| Distinct | 3 |
| Weak | 2 |
| Very weak | 1 |
| Not detectable | 0 |

The arithmetic mean was calculated from the individual results.

The determination of hedonic tone of an odor sample can be taken as an indication of its nuisance effect. As a basis for voting for the hedonic of the emissions, the panel members answered the question:

Assume that you would be exposed to the air of the sample for several hours daily: How pleasant is the air quality?

The emotional effect of the odor is described with the hedonic tone. The hedonic tone describes if the odor will be perceived as pleasant or unpleasant. The assessment was done with whole-numbers from the 9-point scale (see Table 3) from −4 unpleasant to +4 pleasant.

TABLE 3

| Scale for Hedonic Tone | |
|---|---|
| Description | Hedonic Tone |
| Extremely pleasant | +4 |
| Very pleasant | +3 |
| Pleasant | +2 |
| Slightly pleasant | +1 |
| Neither nor | 0 |
| Slightly unpleasant | −1 |

TABLE 3-continued

Scale for Hedonic Tone

| Description | Hedonic Tone |
|---|---|
| Unpleasant | −2 |
| Very unpleasant | −3 |
| Extremely unpleasant | −4 |

From the individual results the arithmetic mean is calculated

Results

The Odor Intensity and Hedonic Tone results are reported below in Table 4.

TABLE 4

Odor intensity and hedonic tone odor

| Sample | Odor Intensity | STD odor Intensity | Hedonic Tone | STD Hedonic Tone |
|---|---|---|---|---|
| 1 | 3.4 | 0.8 | −1.4 | 0.7 |
| 2 | 3.4 | 0.4 | −1.3 | 1.6 |
| 3 | 2.9 | 0.5 | −1.6 | 1.2 |
| 4 | 2.9 | 0.4 | −1.3 | 0.6 |
| 5 (exemplary embodiment of this disclosure) | 2.1 | 0.9 | −0.8 | 0.5 |

The invention claimed is:

1. A wound dressing comprising a liquid permeable wound facing layer, an opposing backing layer, and a layered, interior arrangement positioned therebetween, the interior arrangement including an absorbent core, an active carbon containing layer and a zeolite containing layer, wherein said active carbon containing layer and said zeolite containing layer are arranged between the absorbent core and the backing layer.

2. The wound dressing of claim 1, wherein said active carbon containing layer is positioned between said absorbent core and said zeolite containing layer.

3. The wound dressing of claim 1, wherein said zeolite containing layer is positioned between said absorbent core and said active carbon containing layer.

4. The wound dressing of claim 1, wherein said absorbent core comprises superabsorbent polymer particles.

5. The wound dressing according to claim 1, wherein said active carbon containing layer comprises active carbon particles carried by a first carrier layer.

6. The wound dressing of claim 1, wherein said active carbon containing layer comprises from 30 to 500 g/m² active carbon.

7. The wound dressing according to claim 1, wherein said active carbon containing layer has a thickness of from 0.1 to 5 mm.

8. The wound dressing according to claim 1, wherein said zeolite containing layer comprises zeolite particles carried by a nonwoven or a textile material of natural and/or synthetic fibers.

9. The wound dressing of claim 1, wherein said zeolite containing layer comprises from 0.2 to 10 g/m² zeolite.

10. The wound dressing according to claim 1, wherein said zeolite containing layer has a thickness of from 0.1 to 5 mm.

11. The wound dressing according to claim 1, wherein said active carbon containing layer and said zeolite containing layer together have a thickness of from 0.2 to 5 mm.

12. The wound dressing according to claim 1, wherein said backing layer comprises a polymeric film layer.

13. The wound dressing according to claim 1, wherein said backing layer is stretchable.

14. The wound dressing according to claim 1, wherein said backing layer is vapor permeable and liquid impermeable.

15. The wound dressing according to claim 1, wherein said wound facing layer and said backing layer are joined together by means of a seam forming a perimeter around said interior, layered arrangement.

16. The wound dressing according to claim 15, comprising a bond promotion material positioned between said wound facing layer and said backing layer, at least in said seam.

17. The wound dressing according to claim 15, wherein said seam defines an inner portion, laterally inside said seam, in which inner portion said wound facing layer and said backing layer are not permanently joined together, and wherein the surface area of said absorbent core is smaller than the surface area of said inner portion.

18. The wound dressing of claim 17, where the surface area of said absorbent core is from 40 to 90% of the surface area of said inner portion.

19. The wound dressing according to claim 1, comprising an adhesive disposed on at least part on a wound facing surface of said wound facing layer.

20. A method for the production of a wound dressing including a liquid permeable wound facing layer, an opposing backing layer, and a layered, interior arrangement positioned therebetween, the interior arrangement including an absorbent core, an active carbon containing layer and a zeolite containing layer, the method comprising the steps of
positioning an absorbent core, an active carbon containing layer and a zeolite containing layer between a wound facing layer material, and a backing layer material; and
joining the wound facing layer material to the backing layer material forming a seam encircling the absorbent core, active carbon containing layer and zeolite containing layer,
wherein said active carbon containing layer and said zeolite containing layer are arranged between the absorbent core and the backing layer.

* * * * *